(12) United States Patent
Breeden et al.

(10) Patent No.: US 8,283,493 B2
(45) Date of Patent: Oct. 9, 2012

(54) PROCESS FOR THE PRODUCTION OF ACETIC ACID

(75) Inventors: Clive Richard Breeden, Camerton (GB); Simon Frederick Thomas Froom, Snaith (GB); Sean Anthony Hennigan, Hull (GB); Stephen James Smith, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 12/735,796

(22) PCT Filed: Feb. 11, 2009

(86) PCT No.: PCT/GB2009/000381
§ 371 (c)(1),
(2), (4) Date: Aug. 18, 2010

(87) PCT Pub. No.: WO2009/103948
PCT Pub. Date: Aug. 27, 2009

(65) Prior Publication Data
US 2010/0324333 A1 Dec. 23, 2010

(30) Foreign Application Priority Data
Feb. 19, 2008 (EP) .................................... 08250564

(51) Int. Cl.
*C07C 51/12* (2006.01)
(52) U.S. Cl. ...................................................... 562/519
(58) Field of Classification Search .................. None
See application file for complete search history.

(56) References Cited

U.S. PATENT DOCUMENTS
5,917,089 A * 6/1999 Howard ......................... 562/519
6,617,472 B1 9/2003 Thiebaut et al.
7,202,382 B2 * 4/2007 Muskett ........................ 562/519
7,741,517 B2 * 6/2010 Miller et al. .................. 562/519

FOREIGN PATENT DOCUMENTS
| EP | 0 752 406 | 1/1997 |
| EP | 0 759 419 | 2/1997 |
| WO | WO 03/097567 | 11/2003 |
| WO | WO 03/106396 | 12/2003 |

OTHER PUBLICATIONS

International Search Report for PCT/GB2009/000381, mailed Mar. 19, 2009.
Written Opinion of the International Searching Authority for PCT/GB2009/000381, mailed Mar. 19, 2009.
Howard, M.J. et al., "$C_1$ to acetyls: catalysis and process", Catalysis Today, vol. 18, (1993), pp. 325-354.

* cited by examiner

*Primary Examiner* — Sudhakar Katakam
(74) *Attorney, Agent, or Firm* — Nixon & Vanderhye

(57) ABSTRACT

Process for the production of acetic acid by (a) introducing methanol, methyl acetate, dimethyl ether and/or methyl iodide and carbon monoxide into a first reaction zone containing a liquid reaction composition comprising a carbonylation catalyst, optionally a carbonylation catalyst promoter, methyl iodide, methyl acetate, acetic acid and water, (b) withdrawing at least a portion of the liquid reaction composition together with dissolved and/or entrained carbon monoxide and other gases from the first reaction zone, (c) passing at least a portion of the withdrawn liquid reaction composition to a second reaction zone, wherein at least a portion of the dissolved and/or entrained carbon monoxide is consumed, (d) passing at least a portion of the liquid reaction composition from the second reaction zone into a flash separation zone to form a vapor fraction, which comprises acetic acid, methyl iodide, methyl acetate and low pressure off-gas, comprising carbon monoxide; and a liquid fraction, which comprises carbonylation catalyst and optional carbonylation catalyst promoter, and (e) passing the vapor fraction from the flash separation zone to one or more distillation zones to recover acetic acid product. The temperature of the liquid reaction composition withdrawn from the first reaction zone is in the range of 170 to 195° C.; and the temperature of the liquid reaction composition passed from the second reaction zone to the flash separation zone is at least 8° C. greater than the temperature of the liquid reaction composition withdrawn from the first reaction zone.

22 Claims, 1 Drawing Sheet

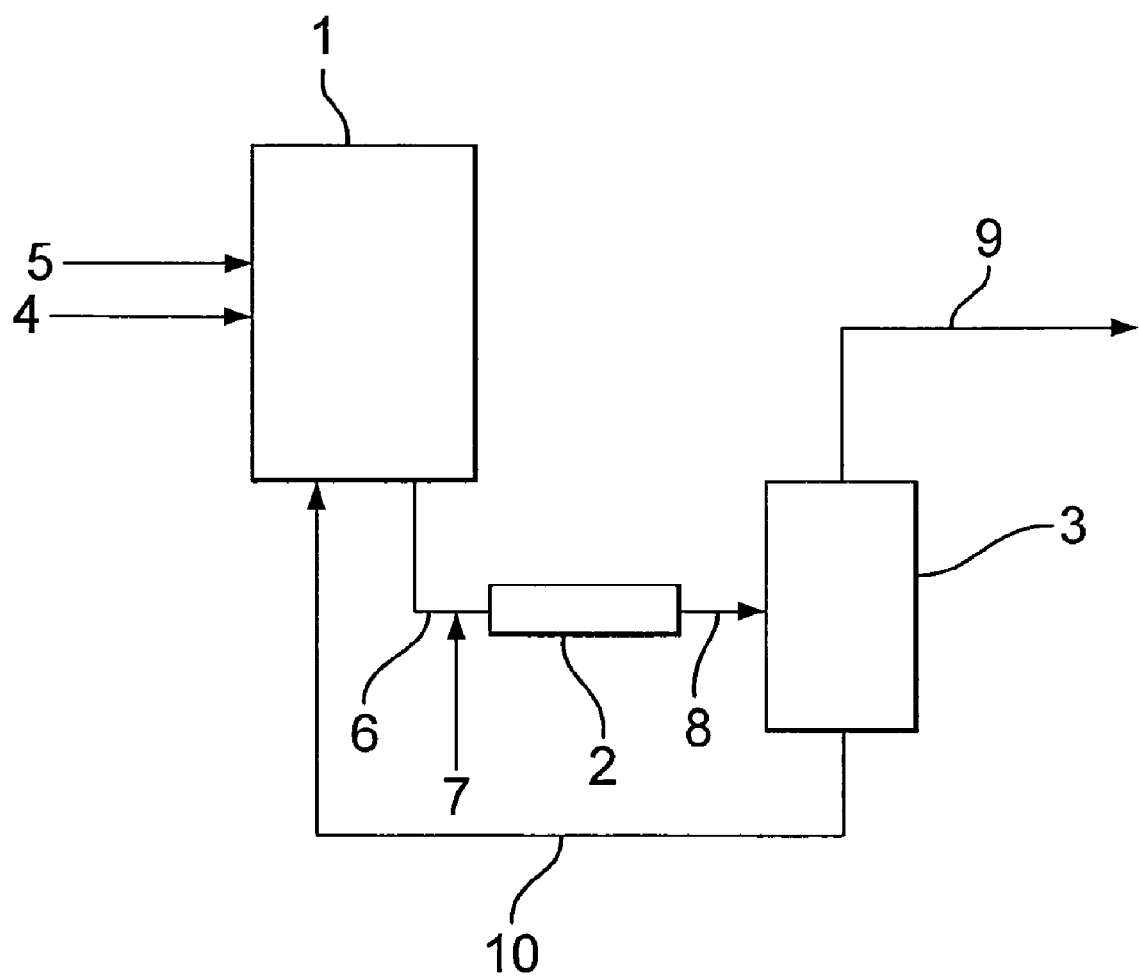

PROCESS FOR THE PRODUCTION OF ACETIC ACID

This application is the U.S. national phase of International Application No. PCT/GB2009/000381 filed 11 Feb. 2009, which designated the U.S. and claims priority to EP Application No. 08250564.5 filed 19 Feb. 2008, the entire contents of each of which are hereby incorporated by reference.

BACKGROUND OF THE INVENTION

The present invention relates to a process for the production of acetic acid by carbonylation of methanol and/or reactive derivative thereof.

SUMMARY OF THE INVENTION

The production of acetic acid by carbonylation of methanol and/or a reactive derivative thereof in the presence of a rhodium catalyst is described in, for example, GB-A-1,233,121, EP 0384652, and EP 0391680. The process in the presence of an iridium catalyst is described in, for example, GB-A-1234641, U.S. Pat. No. 3,772,380, EP 0616997, EP 0618184, EP 0786447, EP 0643034, EP 0752406.

Howard et al in Catalysis Today, 18 (1993), 325-354 describe the general rhodium and iridium-catalysed carbonylation of methanol to acetic acid. The continuous catalysed, homogeneous methanol carbonylation process is said to consist of three basic sections; reaction, purification and off-gas treatment. The reaction section comprises a stirred tank reactor, operated at elevated temperature, and a flash vessel. Liquid reaction composition is withdrawn from the reactor and is passed through a flashing valve to the flash vessel, in which a vapour fraction, comprising condensable components (including product acetic acid) and low-pressure off-gas is separated from a liquid fraction. The vapour fraction is then passed to the purification section whilst the liquid fraction is recycled to the reactor. The purification section is said to comprise a series of distillation columns wherein impurities are removed from the acetic acid product.

EP 0685446 relates to a process for the preparation of acetic acid which comprises carbonylating methanol with carbon monoxide in a first reactor in the presence of a rhodium catalyst. The reaction fluid containing dissolved carbon monoxide is passed from the first reactor to a second reactor where the dissolved carbon monoxide, without the feeding of additional carbon monoxide, is further reacted before the reaction fluid is introduced into a flash zone.

EP 0846674 describes a liquid phase process for the production of carboxylic acid which comprises carbonylating an alkyl alcohol with carbon monoxide in a first reaction zone in the presence of an iridium catalyst wherein at least a portion of the liquid reaction composition together with dissolved and/or entrained carbon monoxide is withdrawn from the first reaction zone and is passed into a second reaction zone, and wherein at least a portion of the dissolved and/or entrained carbon monoxide in the withdrawn reaction composition is reacted by further carbonylation in the second reaction zone to produce further carboxylic acid product, prior to the reaction composition being passed into a flash zone.

Neither EP 0685446 nor EP 0846674 teach or suggest that an increase in temperature across the secondary reactor could have any beneficial effect on the carbonylation process.

It has now been surprisingly found that in the production of acetic acid by the carbonylation of methanol and/or reactive derivative thereof with carbon monoxide a variety of advantages arise when the temperature of the liquid reaction composition is increased on passing the liquid reaction composition through the secondary reactor.

Accordingly, the present invention provides a process for the production of acetic acid which process comprises the steps of:

(a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water;

(b) withdrawing at least a portion of the liquid reaction composition together with dissolved and/or entrained carbon monoxide and other gases from the first reaction zone;

(c) passing at least a portion of the withdrawn, liquid reaction composition to a second reaction zone, wherein at least a portion of the dissolved and/or entrained carbon monoxide is consumed;

(d) passing at least a portion of the liquid reaction composition from the second reaction zone into a flash separation zone to form: a vapour fraction, which comprises acetic acid, methyl iodide, methyl acetate and low pressure off-gas, which low pressure off-gas comprises carbon monoxide; and a liquid fraction, which comprises carbonylation catalyst and optional carbonylation catalyst promoter;

(e) passing the vapour fraction from the flash separation zone to one or more distillation zones to recover acetic acid product;

wherein the temperature of the liquid reaction composition withdrawn from the first reaction zone is in the range of 170 to 195° C.; and the temperature of the liquid reaction composition passed from the second reaction zone to the flash separation zone is at least 8° C. greater than the temperature of the liquid reaction composition withdrawn from the first reaction zone.

In the process of the present invention the temperature of the liquid reaction composition passed from the second reaction zone to the flash separation zone is at least 8° C. greater than the temperature of liquid reaction composition withdrawn from the first reaction zone. This increase in temperature allows improved separation of acetic acid and other condensable components from the carbonylation catalyst and optional carbonylation catalyst promoter in the flash separation zone. Thus, the vapour fraction from the flash separation zone will be richer in acetic acid, thereby allowing a higher yield of acetic acid to be achieved. Further, the volume and flow rate of the liquid fraction will be reduced.

Increasing the temperature of liquid reaction composition after its withdrawal from the first reaction zone and prior to its passage into the flash separation zone allows the first reaction zone to be operated at a lower temperature than might otherwise be employed. Operation of the first reaction zone at a reduced temperature will result in an increased partial pressure of carbon monoxide. This may be advantageous as an increased carbon monoxide partial pressure will result in an increased rate of carbonylation.

Alternatively, where an increased rate of carbonylation is undesirable, the carbon monoxide partial pressure can be maintained, for example, by reducing the rate at which high pressure off-gas is vented from the first reaction zone. This is advantageous since loss of carbon monoxide to the atmosphere is reduced.

Thus, the present invention provides an improved process for the production of acetic acid by carbonylation of methanol and/or reactive derivative thereof. In particular, as described above, yield of acetic acid product is improved, thereby providing a more economical process.

In the process of the present invention, suitable reactive derivatives of methanol include methyl acetate, dimethyl ether and methyl iodide. A mixture of methanol and or reactive derivatives thereof may be used as reactants in the process of the present invention. Preferably, methanol and/or methyl acetate are used as reactants.

Methyl acetate may be formed in situ in the liquid reaction composition by the reaction of methanol and/or reactive derivative thereof with the acetic acid product or solvent. Preferably the concentration of methyl acetate in the liquid reaction composition in the first reaction zone is in the range 2 to 50 wt %, more preferably 3 to 35 wt %.

Preferably, the concentration of methyl iodide in the liquid reaction composition in the first reaction zone is independently in the range of 1 to 20 wt %, preferably 2 to 16 wt %.

The process of the present invention may employ a group VIII noble metal carbonylation catalyst. Preferably, the carbonylation catalyst comprises rhodium, iridium or mixtures thereof. Where the catalyst is rhodium, the optional carbonylation catalyst promoter may be selected from the group consisting of alkali metal iodides, for example lithium iodide, alkaline earth metal iodides, aluminium group metal iodides and/or organic iodide salts. Where the catalyst is iridium; the optional carbonylation catalyst-promoter may be selected from the group consisting of ruthenium, osmium, rhenium, and mixtures thereof.

Where the carbonylation catalyst is iridium, the iridium catalyst may comprise any iridium-containing compound which is soluble in the liquid reaction composition. The iridium catalyst may be added to the liquid reaction composition in any suitable form which dissolves in the liquid reaction composition or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction composition in the first and second reaction zones is independently in the range 100 to 6000 ppm by weight of iridium.

Where the carbonylation catalyst is iridium, the carbonylation catalyst promoter is preferably ruthenium. The promoter may comprise any ruthenium-containing compound which is soluble in the liquid reaction composition. The ruthenium promoter may be added to the liquid reaction composition in any suitable form which dissolves in the liquid reaction composition or is convertible to soluble form. Preferably, the ruthenium promoter compound may be used as chloride-free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, $[Ru(CO)_3I_3]^+$, tetra(aceto)chlororuthenium (II, III), ruthenium (III) acetate, ruthenium (III) propionate, ruthenium(III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium (II), tetrachlorobis(benzene)diruthenium(II), dichloro(cycloocta-1,5-diene)ruthenium (II) polymer and tris(acetylacetonate)ruthenium (III).

Preferably, the ruthenium-containing compounds are free, of impurities which provide or generate in-situ ionic iodides which may inhibit the reaction, for example, alkali or alkaline earth metal or other metal salts.

Preferably, the ruthenium promoter is present in an effective amount up to the limit of its solubility in the liquid reaction composition, the liquid fraction and/or any liquid process streams recycled to the carbonylation reaction zones from the one or more distillation zones.

The ruthenium promoter is suitably present in the liquid reaction composition at a molar ratio of each ruthenium promoter:iridium in the range [0.1 to 100]:1, preferably [greater than 0.5]:1, more preferably [greater than 1]:1 and preferably [up to 20]:1 more preferably [up to 15]:1 and yet more preferably [Up to 10]:1.

The concentration of ruthenium promoter in the liquid reaction composition in each of the first and second reaction zones is, independently, less than 6000 ppm. A suitable promoter concentration is 400 to 5000 ppm, such as 2000 to 4000 ppm.

Suitable rhodium carbonylation catalysts are described, for example, in EP-A-0 161 874, U.S. Pat. No. 6,211,405 and EP-A-0728727.

Where the carbonylation catalyst is rhodium, the rhodium catalyst concentration in the liquid reaction composition is preferably in the range 50 to 5000 ppm, preferably 100 to 1500 ppm by weight of rhodium.

Where rhodium is used as the catalyst, an alkali metal iodide, such as lithium iodide is preferably used as the promoter, as described, for example, in EP-A-0 161 874, U.S. Pat. No. 6,211,405 and EP-A-0728727.

Carbon monoxide is suitably present in the first reaction zone at a partial pressure of $1 \times 10^5$ to $7 \times 10^6$ $Nm^{-2}$, preferably $1 \times 10^5$ to $3.5 \times 10^6$ $Nm^{-2}$.

Water may be formed in situ in the liquid reaction composition, for example, by the esterification reaction of methanol and acetic acid product. Additionally or alternatively, water may be introduced independently to the first reaction zone together with or separately from other components of the liquid reaction composition. Where iridium is used as the carbonylation catalyst the amount of water in the liquid reaction composition in the first reaction zone is suitably at least 0.5 wt % up to maximum of 15 wt %, such as up to 10 wt %, preferably up to 8 wt %. Where rhodium is used as the carbonylation catalyst the amount of water in the first reaction zone is preferably in the range 0.1 to 15 wt %, preferably 1 to 15 wt %, more preferably 1 to 8 wt %.

The first reaction zone may comprise a conventional liquid-phase carbonylation reaction zone. The first reaction zone may be operated at a reaction pressure in the range of $1 \times 10^6$ to $2 \times 10^7$ $Nm^{-2}$, preferably $1.5 \times 10^6$ to $1 \times 10^7$ $Nm^{-2}$, more preferably $1.5 \times 10^6$ to $5 \times 10^6$ $Nm^{-2}$.

In step b) of the process of the present invention at least a portion of the liquid reaction composition together with dissolved and/or entrained carbon monoxide is withdrawn from the first reaction zone, and in step c) at least a portion of the withdrawn liquid and dissolved and/or entrained carbon monoxide is passed to a second reaction zone, wherein the dissolved and/or entrained carbon monoxide is consumed by further carbonylation to produce additional acetic acid. Preferably, substantially all of the liquid reaction composition together with dissolved and/or entrained carbon monoxide withdrawn from the first reaction zone is passed to the second reaction zone.

Preferably, the temperature of the liquid reaction composition withdrawn from the first reaction zone is in the range 185 to 195° C.

The second reaction zone may be operated at a reaction pressure which is substantially the same as that of the first reaction zone.

Preferably, the second reaction zone has a volume in the range of 5 to 20%, more preferably 10 to 20% of the volume of the first reaction zone.

Increasing the temperature of liquid reaction composition after its withdrawal from the first reaction zone and prior to its passage into the flash separation zone can be achieved by the introduction of carbon monoxide into the second reaction zone, in addition to the carbon monoxide which is dissolved and/or entrained in the liquid reaction composition withdrawn from the first reaction zone.

Alternatively or additionally, the temperature increase could be achieved by applying heat to the second reaction zone.

The introduction of additional carbon monoxide into the second reaction zone results in an increased amount of carbonylation taking place therein. In the absence of unreacted methanol, the increased carbonylation results in the consumption of methyl acetate and water present in the liquid reaction composition to form acetic acid. Specifically, one mole of methyl acetate, one mole of water and one mole of carbon monoxide will produce two moles of acetic acid. Such carbonylation of methyl acetate is exothermic; hence, this carbonylation delivers a temperature increase in the second reaction zone.

An appropriate amount of additional carbon monoxide which can be introduced into the second reaction zone is between 0.5 to 20%, preferably 1 to 15%, more preferably 1 to 10%, of the total amount of carbon monoxide introduced into the first reaction zone.

Carbon monoxide is suitably present in the second reaction zone at a partial pressure in the range of $1 \times 10^5$ to $3.5 \times 10^6$ $Nm^{-2}$, preferably $1 \times 10^5$ to $1.5 \times 10^6$ $Nm^{-2}$.

Increased carbonylation in the second reaction zone itself has a number of advantages. In particular, since acetic acid is produced the vapour fraction in the flash separation zone will be even further enriched with acetic acid. Further, since methyl acetate and water are consumed, separation of product acetic acid from light components (which include methyl acetate and water) will require less energy than would otherwise be required.

Alternatively, since methyl acetate and water are consumed in the second reaction zone, the first reaction zone may be operated at higher concentrations of methyl acetate and water without adversely affecting the composition of the liquid reaction composition passed into the flash separation zone; and since the formation of by-products in methanol carbonylation processes tends to decrease with increasing concentrations of methyl acetate and water, operating the first reaction zone at higher concentrations of methyl acetate and water can lead to an overall reduction in by-products.

The total residence time of liquid reaction composition in the second reaction zone is suitably in the range 10 seconds to 5 minutes, preferably 30 seconds to 3 minutes.

Where additional carbon monoxide is introduced into the second reaction zone the additional carbon monoxide may be fed separately to one or more locations within the second reaction zone. Such additional carbon monoxide may contain impurities, such as $H_2$, $N_2$, $CO_2$ and $CH_4$. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

In iridium catalysed, ruthenium promoted carbonylation processes it is preferred that the total amount of carbon monoxide introduced into the first and second reaction zones is sufficient to minimise precipitation of the iridium catalyst and/or ruthenium promoter. According to EP 1506151, maintaining the concentration of carbon monoxide in the low-pressure off-gas, which can be separated from the vapour fraction formed in the flash separation zone in the one or more distillation zones, according to the formula: $Y>mX+C$, wherein Y is the molar concentration of carbon monoxide in the low pressure off-gas, X is the concentration in ppm by weight of ruthenium in the liquid reaction composition, m is about 0.012 and C is about −8.7, minimises precipitation of the catalyst system (that is the iridium catalyst and the ruthenium promoter). In the process of the present invention, it is preferred that the concentration of carbon monoxide in the low-pressure off-gas is about 15 mol % greater than the value of $mX+C$ for every 10° C. rise in the temperature of the liquid reaction composition passed into the flash separation zone compared to the temperature of the liquid reaction composition withdrawn from the first reaction zone.

Preferably, the first and second reaction zones are maintained in separate reaction vessels with means for withdrawing from the first reaction vessel and passing to the second reaction vessel liquid reaction composition with dissolved and/or entrained carbon monoxide. A suitable separate second reaction vessel may comprise a vessel which is capable of acting as a plug-flow reactor. The second reaction vessel may, for example, be a section of pipe between the first reaction vessel and the flash separation zone.

Alternatively, the second reaction vessel may comprise an integrated part of the first reaction vessel, for example, a seal pan. In a further embodiment, the second reaction zone may comprise both an integrated part of the first reaction vessel and a separate second reaction vessel. The design of the second reaction zone is suitably such as to minimise or substantially eliminate back-mixing in the second reaction zone.

Preferably, the concentration of methyl acetate in the liquid reaction composition in the second reaction zone is in the range 2 to 40 wt %, more preferably 2 to 25 wt %.

Wherein the increase in temperature of liquid reaction composition after its withdrawal from the first reaction zone and prior to its passage into the flash separation zone is achieved by the introduction of additional carbon monoxide into the second reaction zone, preferably, the concentration of methyl acetate in the liquid reaction composition passed into the flash separation zone is at least 1.5 wt % less than the concentration of methyl acetate in the liquid reaction composition withdrawn from the first reaction zone.

Where iridium is used as the carbonylation catalyst the amount of water in the liquid reaction composition in the second reaction zone is suitably at least 0.5 wt % up to maximum of 15 wt %, such as up to 10 wt %, preferably up to 8 wt %. Where rhodium is used as the carbonylation catalyst the amount of water in the second reaction zone is preferably in the range 0.1 to 15 wt %, preferably 1 to 15 wt %, more preferably 1 to 8 wt %.

Wherein the increase in temperature of liquid reaction composition after its withdrawal from the first reaction zone and prior to its passage into the flash separation zone is achieved by the introduction of additional carbon monoxide into the second reaction zone, preferably, the concentration of water in the liquid reaction composition passed to the flash separation zone is at least 0.4 wt % less than the concentration of water in the liquid reaction composition withdrawn from the first reaction zone.

Preferably, the concentration of methyl iodide in the liquid reaction composition in the second reaction zone is in the range of 1 to 20 wt %, preferably 2 to 16 wt %.

In step d) of the process of the present invention at least a portion of the liquid reaction composition from step c) is passed to the flash separation zone. Suitably, substantially all of the liquid reaction composition from step c) is passed to the flash separation zone. Alternatively, one or more portions of the liquid reaction composition from step c) may be withdrawn from the second reaction zone and, for example, passed to a waste heat boiler loop.

Preferably, the temperature of the liquid reaction composition passed to the flash separation zone is less than or equal to 215° C. Maintaining the temperature of the liquid reaction composition passed to the flash separation zone at less than or equal to 215° C. may avoid certain disadvantages, such as, decomposition of the carbonylation catalyst and/or carbonylation catalyst promoter.

Preferably, the temperature of the liquid reaction composition passed into the flash separation zone is in the range 195 to 215° C., more preferably 200 to 215° C.

Preferably, the liquid reaction composition passed into the flash separation zone is at a temperature which is 10 to 20° C. greater than the temperature of the liquid reaction composition withdrawn from the first reaction zone.

Liquid reaction composition may be passed into the flash separation zone by means of a flashing valve.

The flash separation zone may comprise an adiabatic flash vessel. Alternatively, the flash separation zone may comprise heating means.

The flash separation zone may be operated at a pressure in the range of 0 to 10 barg, preferably 0 to 3 barg.

Preferably, at least a portion of the liquid fraction from the flash separation zone is recycled to the first reaction zone and/or the second reaction zone.

As described above, improved separation in the flash separation zone results in reduced volume and flow rate of the liquid fraction. Thus, where at least a portion of the liquid fraction is recycled to the first reaction zone, the reduced flow rate of the liquid fraction will result in decreased cooling in the first reaction zone. Decreased cooling in the first reaction zone may allow heat, which might otherwise be wasted, to be usefully exploited; thereby reducing the energy requirements of the process. Further, since the flow rate of the liquid fraction is reduced the flow rates of the liquid reaction composition passing from the first reaction zone to the second reaction zone and the liquid reaction composition passing from the second reaction zone to the flash separation zone will also be reduced. As a result, the amount of carbonylation catalyst and optional carbonylation catalyst promoter passed to the flash separation zone per unit of time will be reduced; and, as the vapour fraction is enriched in acetic acid, the amount of catalyst and optional promoter passed to the flash separation zone per unit of acetic acid produced will also be reduced.

In step e) of the process acetic acid product is recovered from the vapour fraction from the flash separation zone by distillation. The distillation zone can be any conventional distillation apparatus used in the production of acetic acid. For example, the distillation zone may comprise a first distillation column in which acetic acid product is separated from light components, such as methyl iodide and methyl acetate. The light components are removed overhead and may be recycled to the first or second reaction zones. Also removed overhead is a low pressure off-gas comprising the non-condensable gases such as nitrogen, carbon monoxide, hydrogen and carbon dioxide. Such a low-pressure off-gas stream may be passed through an off-gas treatment section to remove any condensable materials such as methyl iodide, prior to being vented to atmosphere, for example, via a flare. The distillation zone may comprise further distillation columns to remove further impurities, such as water and higher-boiling by-products, from the product acetic acid.

The temperature of the liquid reaction composition withdrawn from the primary reaction zone may be measured at the outlet of the first reaction zone through which liquid reaction composition is withdrawn.

The temperature of the liquid reaction composition passed from the second reaction zone to the flash separation zone may be measured at the inlet of the flash separation zone through which liquid reaction composition is passed. Where liquid reaction composition is passed into the flash separation zone by means of a flashing valve, the temperature of the liquid reaction composition passed from the second reaction zone may be measured at the flashing valve.

The process of the present invention may be performed as a batch or a continuous process, preferably as a continuous process.

BRIEF DESCRIPTION OF THE DRAWINGS

The process of the present invention will now be illustrated by the following non-limiting examples and with reference to FIG. 1.

FIG. 1 represents in schematic form, apparatus suitable for carrying out the process of the present invention.

DETAILED DESCRIPTION OF PREFERRED EMBODIMENTS

The apparatus comprises a first reaction zone (1) a second reaction zone (2), a flash separation zone (3) and a combined light ends and drying distillation column (not shown). In use, methanol and carbon monoxide are fed to the first reaction zone (1) via lines (4) and (5) respectively. In the first reaction zone (1) carbon monoxide is contacted with a liquid reaction composition which comprises the carbonylation catalyst, optional carbonylation catalyst promoter, methanol, methyl acetate, water, methyl iodide and acetic acid. Liquid reaction composition is withdrawn from the first reaction zone (1) via line (6), and is passed to the second reaction zone (2), into which an additional supply of carbon monoxide is fed via line (7). The liquid reaction composition from the second reaction zone (2) is passed to flash separation zone (3), via a flashing valve (8) wherein it is separated into two phases: a vapour fraction and a liquid fraction. The vapour fraction comprising acetic acid, methyl iodide, water, methanol and methyl acetate, is fed via line (9) to a distillation zone, comprising a combined light ends and drying column (not shown), from which low pressure off-gas is removed, for recovery of purified acetic acid. The liquid fraction, comprising catalytic species and acetic acid, is returned to the first reaction zone (1) via line (10).

In the following examples acetic acid was produced by carbonylating methanol with carbon monoxide in the presence of an iridium catalyst and ruthenium promoter, using the apparatus of FIG. 1. The first reaction zone (1) comprised a 6 liter primary carbonylation stirred tank reactor, the second reaction zone (2) comprised a secondary plug-flow reactor equipped with heaters, having a volume of approximately 12% of the volume of the primary reactor, and the flash separation zone (3) comprised an adiabatic flash vessel. The operating pressure of the primary reactor was 27.6 barg ($2.76 \times 10^6$ Nm$^2$), and the temperature of the primary reactor was maintained at approximately 190° C. The primary reactor was fitted with a stirrer/propeller and a baffle cage to ensure intimate mixing of the liquid and gaseous reactants. Carbon monoxide was supplied from pressure bottles to the primary reactor via a sparge fitted beneath the stirrer. To minimise iron ingress into the primary reactor (1) the carbon monoxide was passed through a carbon filter (not shown). A jacket (not shown), through which hot oil is circulated, enabled the liquid reaction composition in the primary reactor (1) to be maintained at a constant reaction temperature. The adiabatic flash vessel was operated at a pressure of 1.48 barg ($1.48 \times 10^5$ Nm$^{-2}$). The carbon monoxide concentration in the low-pressure off-gas removed from the combined light-ends and drying column, was maintained at 50-55 mol %. The liquid reaction composition was analysed, at the flash valve, by near infra-red spectroscopy every 4 minutes, and by gas chromatography up to 3 times a day. A high pressure off-gas was purged from the head of the primary reactor.

Using the above-described apparatus, method and operating conditions, but excluding the use of the secondary reactor, a baseline experiment (Experiment A) was performed in which the liquid reaction composition in the primary reactor was maintained at 5 wt % water, 7 wt % methyl iodide and 12 wt % methyl acetate. The temperature of the liquid reaction composition in the primary reactor and at the flash valve, liquid reaction composition data, and the flow rates of various process streams are given in Table 1.

Once the baseline experiment had been completed the secondary reactor was brought online and the carbonylation rate increased by the addition of iridium and ruthenium to line (10) to give a production rate of approximately 5.8 kg·h$^{-1}$. The temperature of the liquid reaction composition withdrawn from the first reaction zone was maintained at approximately 190° C. and the temperature of liquid reaction composition passed to the flash separation zone was maintained at approximately 210° C. The process was operated under these conditions for 8 weeks. The temperature of the liquid reaction composition in the primary reactor and at the flash valve, liquid reaction composition data, and the flow rates of various process streams after 3 weeks (Example 1) and after 5 weeks (Example 2) are given in Table 1. After operation of the process for 8 weeks the plant was shut down and the surfaces of the apparatus which had come into to contact with liquid reaction composition were visually inspected for deposits and signs of corrosion. Examples 1 and 2 are examples according to the present invention.

Once the visual inspection had been completed the plant was restarted and controlled to give a production rate of approximately 4.6 kg·h$^{-1}$. The temperature of the liquid reaction composition withdrawn from the first reaction zone was maintained at approximately 190° C. and the temperature of liquid reaction composition passed to the flash separation zone was maintained at approximately 230° C. The process was operated under these conditions for 4 weeks. The temperature of the liquid reaction composition in the primary reactor and at the flash valve, liquid reaction composition data and the flow rates of various process streams at 3 days (Example 3) and 2 days (Example 4) before the end of the trial are given in Table 1. After operating the process for 4 weeks, the plant was shut down and the surfaces of the apparatus which had come into to contact with the liquid reaction composition were inspected for deposits and signs of corrosion.

It can be seen from Table 1 that in Examples 1, 2, 3 and 4 the flow rate of the liquid fraction decreased after the secondary reactor was brought online. This demonstrates that the temperature increase across the secondary reactor allows improved separation of condensables from the catalyst and promoter.

It can also be seen from Table 1 that in Examples 1, 2, 3 and 4 the concentration of acetic acid present in the vapour fraction increased after the secondary reactor was brought online. This demonstrates that the process of the present invention allows an increased yield of acetic acid product to be achieved.

In addition, it can be seen from Table 1 that in Examples 1, 2, 3 and 4 the concentration ratio of acetic acid to methyl acetate and water in the liquid reaction composition passed into the flash vessel increased after the secondary reactor was brought online. This demonstrates that further carbonylation is taking place in the secondary reactor.

It can further be seen from Table 1 that in Examples 1, 2, 3 and 4 the flow rate of the liquid reaction composition passed into the flash vessel decreased after the secondary reactor was brought online. This demonstrates that the amount of catalyst and promoter passing into the flash vessel per unit of acetic acid product is reduced.

After completion of the 8 week operation of the process wherein the temperature of the liquid reaction composition at the flash valve was maintained at approximately 210° C., the surfaces of the apparatus which had come into contact with the liquid reaction composition retained their original appearance.

After completion of the 4 week operation of the process wherein the temperature of the liquid reaction composition at the flash valve was maintained at approximately 230° C., dark marks were present of the surfaces of the apparatus which had come into contact with the liquid reaction composition, suggesting that decomposition of the catalyst and/or promoter might have occurred.

TABLE 1

| Example | Temperature (° C.) | | Liquid reaction composition at flash valve | | | | | AcOH in liquid fraction (wt %) |
|---|---|---|---|---|---|---|---|---|
| | 1$^{st}$ reaction zone | At flash valve | Molar Ratio of Ru:Ir | H$_2$O (wt %) | MeI (wt %) | MeOAc (wt %) | AcOH (wt %) | |
| A | 190.0 | 188.3 | 3.78:1 | 4.9 | 6.8 | 11.3 | 74.5 | 83.6 |
| 1 | 190.4 | 209.5 | 1.52:1 | 4.0 | 6.7 | 10.3 | 74.5 | 84.1 |
| 2 | 190.1 | 209.3 | 1.95:1 | 4.0 | 7.0 | 10.0 | 75.1 | 85.9 |
| 3 | 191.1 | 229.5 | 1.38:1 | 4.8 | 5.2 | 5.7 | 82.0 | 87.7 |

TABLE 1-continued

| | | | | | | | | |
|---|---|---|---|---|---|---|---|---|
| 4 | 190.6 | 230.0 | 1.39:1 | 4.8 | 5.8 | 5.8 | 81.9 | 88.1 |

| | AcOH in vapour fraction (wt %) | Flow rates (kg·h⁻¹) | | | | |
|---|---|---|---|---|---|---|
| Example | | CO to 2nd reaction zone | Flow to flash tank | Liquid fraction | Vapour fraction | Product from base of combined light ends/drying column |
| A | 51.8 | n/a | 28.4 | 20.1 | 8.4 | 4.4 |
| 1 | 59.7 | 0.22 | 24.4 | 14.5 | 10.0 | 6.0 |
| 2 | 61.8 | 0.32 | 19.8 | 10.7 | 9.2 | 5.6 |
| 3 | 67.7 | 0.52 | 21.4 | 15.0 | 6.5 | 4.6 |
| 4 | 65.4 | 0.50 | 24.4 | 17.5 | 6.9 | 4.7 |

The invention claimed is:

1. A process for the production of acetic acid which process comprises the steps of:
   (a) introducing methanol, methyl acetate, dimethyl ether and/or methyl iodide and carbon monoxide into a first reaction zone containing a liquid reaction composition comprising a carbonylation catalyst, optionally a carbonylation catalyst promoter, methyl iodide, methyl acetate, acetic acid and water;
   (b) withdrawing at least a portion of the liquid reaction composition together with dissolved and/or entrained carbon monoxide and other gases from the first reaction zone;
   (c) passing at least a portion of the withdrawn liquid reaction composition to a second reaction zone, wherein at least a portion of the dissolved and/or entrained carbon monoxide is consumed;
   (d) passing at least a portion of the liquid reaction composition from the second reaction zone into a flash separation zone to form a vapour fraction, which comprises acetic acid, methyl iodide, methyl acetate and low pressure off-gas, comprising carbon monoxide; and a liquid fraction, which comprises carbonylation catalyst and optional carbonylation catalyst promoter;
   (e) passing the vapour fraction from the flash separation zone to one or more distillation zones to recover acetic acid product;
   (f) recycling at least a portion of the liquid fraction from the flash separation zone to the first reaction zone;
   wherein the temperature of the liquid reaction composition withdrawn from the first reaction zone is in the range of 170 to 195° C.; and the temperature of the liquid reaction composition passed from the second reaction zone to the flash separation zone is at least 8° C. greater than the temperature of the liquid reaction composition withdrawn from the first reaction zone.

2. A process as claimed in claim 1 wherein the carbonylation catalyst is iridium.

3. A process as claimed in claim 2 wherein the carbonylation catalyst promoter is selected from the group consisting of ruthenium, osmium and rhenium.

4. A process as claimed in claim 3 wherein the carbonylation catalyst promoter is ruthenium.

5. A process as claimed in claim 1 wherein the carbonylation catalyst is rhodium.

6. A process as claimed in claim 1 wherein the temperature of the liquid reaction composition withdrawn from the first reaction zone is in the range 185 to 195° C.

7. A process as claimed in claim 1 wherein the second reaction zone has a volume in the range of 5 to 20% of the volume of the first reaction zone.

8. A process as claimed in claim 1 wherein carbon monoxide, in addition to that dissolved and/or entrained in the liquid reaction composition withdrawn from the first reaction zone, is introduced into the second reaction zone.

9. A process as claimed in claim 6 wherein carbon monoxide, in addition to that dissolved and/or entrained in the liquid reaction composition withdrawn from the first reaction zone, is introduced into the second reaction zone.

10. A process as claimed in claim 8 wherein the amount of additional carbon monoxide introduced into the second reaction zone is between 0.5 to 20% of the amount of carbon monoxide which is introduced into the first reaction zone.

11. A process as claimed in claim 9 wherein the amount of additional carbon monoxide introduced into the second reaction zone is between 0.5 to 20% of the amount of carbon monoxide which is introduced into the first reaction zone.

12. A process as claimed in claim 1 wherein heat is applied to the second reaction zone.

13. A process as claimed in claim 4 wherein the concentration of carbon monoxide in the low-pressure off-gas is about 15 mol % greater than the value of mX+C for every 10° C. rise in the temperature of the liquid reaction composition passed to the flash separation zone compared to the temperature of the liquid reaction composition withdrawn from the first reaction zone, wherein X is the concentration in ppm by weight of ruthenium in the liquid reaction composition, m is about 0.012 and C is about −8.7.

14. A process as claimed in claim 8 wherein the concentration of methyl acetate in the liquid reaction composition passed to the flash separation zone is at least 1.5 wt % less than the concentration of methyl acetate in the liquid reaction composition withdrawn from the first reaction zone.

15. A process as claimed in claim 8 wherein the concentration of water in the liquid reaction composition passed to the flash separation zone is at least 0.4 wt % less than the concentration of water in the liquid reaction composition withdrawn from the first reaction zone.

16. A process as claimed in claim 1 wherein the temperature of the liquid reaction composition passed to the flash separation zone is less than or equal to 215° C.

17. A process as claimed in claim 6 wherein the temperature of the liquid reaction composition passed to the flash separation zone is less than or equal to 215° C.

18. A process as claimed in claim 16 wherein the temperature of the liquid reaction composition passed to the flash separation zone is in the range 195 to 215° C.

19. A process as claimed in claim 17 wherein the temperature of the liquid reaction composition passed to the flash separation zone is in the range 195 to 215° C.

20. A process as claimed in claim 1 wherein the temperature of the liquid reaction composition passed to the flash separation zone is 10 to 20° C. greater than the temperature of the liquid reaction composition withdrawn from the first reaction zone.

21. A process as claimed in claim 6 wherein the temperature of the liquid reaction composition passed to the flash separation zone is 10 to 20° C. greater than the temperature of the liquid reaction composition withdrawn from the first reaction zone.

22. A process as claimed in claim 7 wherein the second reaction zone has a volume in the range of 10 to 20% of the volume of the first reaction zone.

\* \* \* \* \*